United States Patent [19]

Berger

[11] 4,150,141
[45] Apr. 17, 1979

[54] TREATMENT FOR SCABIES

[75] Inventor: Richard S. Berger, Plainsboro, N.J.

[73] Assignee: Johnson & Johnson, New Brunswick, N.J.

[21] Appl. No.: 810,694

[22] Filed: Jun. 28, 1977

[51] Int. Cl.² .......................................... A61K 31/425
[52] U.S. Cl. .................................................... 424/270
[58] Field of Search ........................................ 424/270

[56] References Cited
U.S. PATENT DOCUMENTS 3,274,209  9/1966  Raeymackers et al. ............. 424/270
3,463,786  8/1969  Bullock ................................ 424/270

Primary Examiner—Jerome D. Goldberg

[57] ABSTRACT

Levamisole, a known anthelmintic, is effective in treating scabies when given systemically at dosage levels of about 2.5 mg/kg/day, two consecutive days per week until the patient is disease free. From one to four weeks of such treatment has been found to be generally adequate for cure, without causing significant side effects. Topical treatment with levamisole in a suitable vehicle may be used as an alternative to systemic treatment.

12 Claims, No Drawings

TREATMENT FOR SCABIES

BACKGROUND OF THE INVENTION

1. Field of the Invention

The present invention relates to a treatment for scabies in humans and other mammals. More particularly, it relates to the use of an anthelmintic, levamisole, as well as its racemate, tetramisole, and the pharmaceutically acceptable acid addition salts thereof, to treat this condition.

The mite, Sarcoptes scabiei, is the cause of scabies. It burrows under the upper layer of the skin, producing an inflammatory response and intense itching. The cutaneous diagnostic signs include multiple papules, minute vesicles and occasional linear tracts.

The transmission of scabies has always been associated with close personal contact, and no age or socioeconomic group escapes the disease. The presence of scabies as a disease affecting humans occurs in thirty year cycles.

2. Description of the Prior Art

The treatment of scabies is usually accomplished by the application of medicaments to the skin. Gamma benzene hexachloride is the most extensively used scabicide. Other drugs used are crotamiton, benzyl benzoate and sulfur. Although each of these drugs is effective in the treatment of scabies, each has its shortcomings; gamma benzene hexachloride is not rapidly antipruritic, scabies mites are becoming relatively resistant to it, and it has the potential for being toxic to the central nervous system of infants; crotamiton is sensitizing; and sulfur is unpleasantly odoriferous and stains.

A communication from S. P. Roy Chowdhury appearing at page 152 of the Jan. 15, 1977, edition of The Lancet indicates that the antibacterial drug, nitrofurazone, 0.2% w/w in a water soluble base, was also found to be effective in controlling scabies. Nitrofurazone, also known as nitrofurantoin, is 1-[(5-Nitro-2-furfurylidene)amino] hydantoin, with the structure:

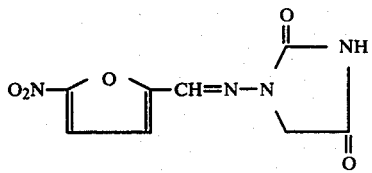

In Arch Dermatol Vol. 112, Oct. 1976, there is reported successful treatment of scabies with the known anthelmintic and fungicide, thiabendazole, both orally and topically. The more recent, topical treatment was not found to induce any local or systemic adverse reactions in contrast to the systemic treatment's side effects: nausea, diarrhea and dizziness. Thiabendazole is 2-(4-thiazolyl)benzimidazole and has the structure:

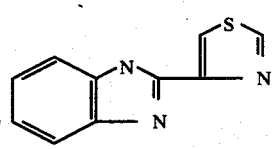

SUMMARY OF THE INVENTION

I have now discovered that levamisole may be used to provide a safe and effective treatment for scabies.

Thus, the present invention provides a method of treating scabies in a mammal which comprises administering to the mammal, in a pharmaceutically acceptable dosage form, an amount of levamisole effective to combat scabies.

DESCRIPTION OF THE PREFERRED EMBODIMENTS

As already mentioned, levamisole, (S) - (-)-2,3,5,6-tetrahydro-6-phenylimidazo [2, 1-b] thiazole, with the following structure:

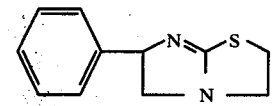

used in accordance with the present invention for the treatment of scabies in humans and other mammals, has been in use around the world for years as an anthelmintic, with few or no adverse side effects. While no accepted theory for its effectiveness against scabies has yet been proven, one theory postulated herein is that this activity may be related to its recently reported ability to restore host resistance, as discussed in several of the publications cited above. Thus, for example, at the International Conference on Scabies, held at the Mayo Memorial Auditorium of the University of Minnesota on May 22-23, 1976, it was suggested that immune system incompetence may play a role in the pathogenesis of scabies. On the other hand, levamisole may act directly on the mite, i.e. as a scabicide.

As used herein, levamisole is intended to include not only the isolated, levorotatory base or its commonly used hydrochloride, but also other pharmaceutically acceptable acid addition salts thereof as well as admixtures thereof with its dextrorotatory optical isomer (and pharmaceutically acceptable salts thereof) as in the racemate, tetramisole.

As indicated in U.S. Pat. No. 3,274,209, issued Sept. 20, 1966, the contents of which are hereby incorporated herein by reference, the free base forms of tetramisole and levamisole are convertible to therapeutically active non-toxic acid addition salts by treatment with an appropriate acid, such as, for example, an inorganic acid, such as, hydrohalic acid. Specific examples of suitable acid salts include the salts obtained from hydrochloric, hydrobromic, hydroiodic, sulfuric, nitric and thiocyanic acid as well as the phosphoric acids. Also included are those obtained by treatment with a suitable organic acid, for example, acetic, propionic, glycolic, lactic, pyruvic, oxalic, malonic, succinic, maleic, fumaric, malic, tartaric, citric, benzoic, cinnamic, mandelic, methanesulfuric, ethanesulfuric, hydroxyethanesulfonic, benzene-sulfonic, p-toluenesulfonic, salicylic, p-aminosalicylic, 2-phenoxybenzoic and 2-acetoxybenzoic acid. Conversely, the salt form can be converted in the usual manner into the free base.

All such salts (as well as the free base) are suitable for use in the method of the present invention.

Other therapeutically acceptable salts, such as the 10-camphor sulfonate salts used to resolve the racemate in accordance with the disclosure of U.S. Pat. No. 3,463,786, may also be used.

In a presently preferred embodiment of the present invention, levamisole hydrochloride is administered orally in tablet form at a dosage level of 2.5 mg/kg/day, for two consecutive days each week, until the patient becomes disease free. Other suitable systemic treatments include capsules, powders, solutions, syrups, etc.

The dosage level may be adjusted as needed. Generally, it will vary from about 1 mg/kg/day to about 5 mg/kg/day.

While any compatible, pharmaceutically acceptable, form and formulation for systemic administration may be used, for example, typical capsule, powder, solution and syrup formulations, a presently preferred composition for administering levamisole systemically is a tablet. Suitable tablet formulations include:

I. Filmtablets (50 mg)

Tablet core:

| | | |
|---|---|---|
| Levamisole hydrochloride | 59 | mg |
| Microcrystalline cellulose (NF XIV) | 42 | mg |
| Lactose (USP XIX) | 7 | mg |
| Hydrogenated vegetable oil (USP XIX) | 1.7 | mg |
| Colloidal silicone dioxide (NF XIV) | 0.3 | mg |
| Total weight | 110 | mg |

The tablet may be film coated with any pharmaceutically acceptable film using art-recognized methods.

II. Tablets 20 mg

| | | |
|---|---|---|
| Levamisole hydrochloride | 23.6 | mg |
| Lactose monohydrate (USP XIX) | 188.9 | mg |
| Microcrystalline cellulose (NF XIV) | 12.5 | mg |
| Talc (USP XIX) | 5 | mg |
| Polyvinylpyrrolidone (FP IX) | 3.75 | mg |
| Magnesium stearate (USP XIX) | 1.25 | mg |
| Sunset yellow (FP VIII) | 0.025 | mg |
| Total weight | 235.025 | mg |

A suitable oral solution formulation is as follows:

| | | |
|---|---|---|
| Levamisole hydrochloride | 5.9 | mg |
| Methylparaben | 0.5 | mg |
| Ethanol | 0.02 | mg |
| Citric acid monohydrate | 0.6 | mg |
| Sorbitol 70% q.s.ad | 1 | ml |

The foregoing formulations can be prepared by suitable art-recognized techniques.

Suitable dosage forms for topical administration of levamisole include creams, gels, solutions, ointments, aerosol sprays, dusting powder, shampoos and bar soaps.

The following formulation represents a typical pharmaceutical cream dosage form that may be used for topical administration of levamisole.

| | | | |
|---|---|---|---|
| Active Ingredient - (levamisole base) | | 10.0 | mg |
| Lipid Phase | Cetyl alcohol | 28.0 | mg |
| | Aldo (Stearyl alcohol) | 84.0 | mg |
| | Miglyol 812 (Caprylic/caproic triglyceride) | 60.0 | mg |
| Emulsifiers o/w | Span 60 (Sorbitan Stearate) | 6.0 | mg |
| | Tween 80 (Polysorbate) | 10.0 | mg |
| Preservatives & Stabilizers | BHA [butylated hydroxyanisole] | 0.52 | mg |
| | Methylparaben | 2.4 | mg |
| | Propylparaben | 0.4 | mg |
| | EDTA [ethylene diamine tetraacetic acid] | 1.0 | mg |
| Aqueous phase | Acetic acid to pH 5 | | |
| | Propylene glycol | 100.0 | mg |
| | Purified water | 698.0 | mg |

The cream formulation may be prepared by any method of manufacture typically employed in the art for an oil-in-water emulsion-type vehicle. In general, the lipid phase ingredients are heated in a suitable container to insure melting while the aqueous phase ingredients are similarly heated in a suitable container, to the same temperature as the oil phase. The two phases are combined with agitation and allowed to cool to the congealing point. The active ingredient (levamisole) is dissolved in a portion of the solvent system and added to the emulsified vehicle and mixed well to insure homogeniety. The finished product is cooled to room temperature and packaged. Other topical dosage forms may be prepared in accordance with the skill of the art.

The following example is presented to further illustrate the present invention without limiting the scope thereof.

EXAMPLE

In an open pilot study with 25 patients suffering from scabies, levamisole was administered orally at a dosage level of 2.5 mg/kg/day (in 50 mg tablets) for two consecutive days each week until cure was achieved. Most patients were free of disease within a week, and the maximum duration of treatment was four weeks.

Twenty-three of the twenty-five patients evaluated achieved good or excellent results, i.e. there was a complete elmination of the mites as well as a dramatic improvement in clinical symptoms.

The following table summarizes the evaluation of 25 patients.

| SCABIES TREATED WITH LEVAMISOLE | | | |
|---|---|---|---|
| Patient | Age | Response | Weeks of Therapy to Cure |
| 1. H.H. | 29 F | E | 2 |
| 2. M.G. | 34 M | G | 4 |
| 3. B.D. | 57 M | E | 1 |
| 4. T.M. | 17 F | E | 3 |
| 5. G.M. | 22 F | E | 3 |
| 6. L.T. | 21 F | W | 2* |
| 7. P.C. | 10 F | E | 1 |
| 8. D.C. | 46 M | E | 1 |
| 9. V.B. | 29 M | E | 1 |
| 10. N.M. | 6 F | E | 1 |
| 11. L.G. | 8 M | E | 1 |
| 12. A.P. | 76 F | E | 1 |
| 13. G.H. | 30 M | G | 1 |
| 14. M.S. | 79 F | E | |
| 15. H.P. | 45 F | E | 1 |
| 16. M.S. | 16 F | E | 1 |
| 17. M.S. | 42 F | G | 3** |
| 18. G.B. | 27 F | P | 3 |
| 19. J.Q. | 36 M | E | 1 |
| 20. F.H. | 57 F | E | 1 |
| 21. J.F. | 22 M | G | 2 |
| 22. C.H. | 28 F | G | 2 |
| 23. A.J. | 48 F | E | 1 |
| 24. P.W. | 16 M | G | 2 |

-continued

SCABIES TREATED WITH LEVAMISOLE

| Patient | Age | Response | Weeks of Therapy to Cure |
|---------|-----|----------|--------------------------|
| 25. D.H. | 7 F | E | 1 |

Note:
E = excellent — generally cleared with one week's treatment
G = good — complete elimination of mites with 2-3 week's treatment
P = poor response
W = worse
*Discontinued by investigator after two weeks
**Patient had severe case of Down Syndrome, did not respond well and was discontinued after three weeks.

Variations can, of course, be made without departing from the spirit and scope of the invention.

Having thus described our invention, what we desire to secure by Letters Patent and hereby claim is:

1. A method of treating scabies in a mammal comprising administering to a mammal in need of said treatment, in a pharmaceutically acceptable vehicle, an effective amount to combat scabies of a levamisole compound selected from the group consisting of levamisole base and the therapeutically acceptable acid addition salts thereof.

2. The method of claim 1 wherein said levamisole compound is administered systemically.

3. The method of claim 2 wherein said levamisole compound dosage administered is about 2.5 mg/kg/day.

4. The method of claim 3 wherein said levamisole compound is administered for two consecutive days per week.

5. The method of claim 4, wherein said treatment is continued for from 1 to about 5 weeks.

6. The method of claim 1 wherein said levamisole compound is administered topically.

7. The method of claim 1 wherein said levamisole compound is administered in the form of the hydrochloride.

8. The method of claim 1 wherein said levamisole compound is administered in the form of the racemic mixture, tetramisole.

9. A topical composition for the treatment of scabies comprising a pharmaceutically acceptable topical cream vehicle containing an effective concentration to combat scabies of levamisole base or a therapeutically acceptable acid addition salt thereof.

10. The topical composition of claim 9 which comprises levamisole.

11. The topical composition of claim 9 which comprises tetramisole.

12. The topical composition of claim 9 which comprises about 1% by weight of levamisole base in a cream vehicle.

* * * * *